United States Patent [19]

Winston

[11] Patent Number: 5,432,146
[45] Date of Patent: Jul. 11, 1995

[54] FREE-FLOWING BICARBONATE FUNGICIDE COMPOSITIONS

[75] Inventor: Anthony E. Winston, East Brunswick, N.J.

[73] Assignee: Church & Dwight Co., Inc., Princeton, N.J.

[21] Appl. No.: 169,638

[22] Filed: Dec. 20, 1993

Related U.S. Application Data

[60] Division of Ser. No. 52,254, Apr. 23, 1993, which is a continuation-in-part of Ser. No. 984,532, Dec. 2, 1992, abandoned.

[51] Int. Cl.$^6$ ............ A01N 37/02; A01N 37/06; A01N 59/00; C05G 3/02
[52] U.S. Cl. .................. 504/101; 424/715; 424/716; 424/717; 71/DIG. 1; 514/557; 514/558; 514/560; 514/770; 514/772; 514/773; 514/774; 514/775; 514/776; 514/777; 514/778; 514/779; 514/780; 514/781; 514/782; 514/784
[58] Field of Search .............. 424/717, 715, 716; 514/558, 560, 557, 770, 772, 773, 774, 775, 776, 777, 778, 779, 780, 781, 782, 784; 504/101; 71/DIG. 1

[56] References Cited

U.S. PATENT DOCUMENTS

| | | | |
|---|---|---|---|
| 3,635,690 | 1/1972 | Griffith | 71/1 |
| 3,931,413 | 1/1976 | Frick et al. | 514/558 |
| 4,424,213 | 1/1984 | Magee et al. | 514/228.2 |
| 4,599,233 | 7/1986 | Misato et al. | 424/717 |
| 4,692,466 | 9/1987 | Yoshimoto et al. | 514/604 |
| 5,030,658 | 7/1991 | Salloum et al. | 514/560 |
| 5,057,326 | 10/1991 | Sampson | 424/711 |
| 5,093,124 | 3/1992 | Kulenkampff | 424/406 |

FOREIGN PATENT DOCUMENTS 5396319  8/1978  Japan .

OTHER PUBLICATIONS

Farm Chemicals Handbook '87, Willoughby (Ohio), Meister Publishing Co., 1987, pp. B16, B17, B34, B54, B56, C228 and C236.

Primary Examiner—Allen J. Robinson
Assistant Examiner—John D. Pak
Attorney, Agent, or Firm—Charles B. Barris

[57] ABSTRACT

The present invention provides a fungicidal fertilizer composition which contains ingredients which are biocompatible for purposes of agricultural applications, and which are harmless to animals and humans. An invention fungicide composition in the form of a dry blend formulation remains non-caking and free-flowing under storage conditions. Illustrative of an invention fungicide composition is a formulation which has a content of sodium bicarbonate, potassium bicarbonate, potassium oleate, xanthan gum and a fertilizer-effective content of nitrogen, phosphorus and potassium elements. The combination of potassium oleate and xanthan gum functions as an effective spreader-sticker and film-forming medium when the composition is diluted with water for agricultural applications. When the aqueous medium is hard water, calcium oleate is formed which enhances the sticker properties of the aqueous fungicide composition in agricultural applications.

5 Claims, No Drawings ated with 5,432,146

FREE-FLOWING BICARBONATE FUNGICIDE COMPOSITIONS

This application is a Division of application Ser. No. 08/052254, filed Apr. 23, 1993, which is a continuation-in-part of application Ser. No. 07/984532, filed Dec. 2, 1992, now abandoned.

BACKGROUND OF THE INVENTION

The control of phytopathogenic fungi is of great economic importance since fungal growth on plants or on parts of plants inhibits production of foliage, fruit or seed, and the overall quality of a cultivated crop.

Because of the vast economic ramifications of fungal propagation in agricultural and horticultural cultivations, a broad spectrum of fungicidal and fungistatic products have been developed for general and specific applications.

Of particular interest with respect to the present invention embodiments are fungicide compositions which contain an inorganic bicarbonate or carbonate compound. It is known that bicarbonate and carbonate compounds exhibit fungicidal properties for agricultural purposes.

Phytopathology, 48, 169 (193) by R. H. Marloth describes studies involving the physiology of fungi. The reference reports studies which demonstrate that sodium and potassium bicarbonate and carbonate salts are toxic to fungi such as *Penicillium italicum* and *Penicillium digitalum*.

U.S. Pat. No. 1,560,558 discloses the use of salts such as lithium carbonate, sodium carbonate, sodium bicarbonate, potassium bicarbonate, potassium carbonate and ammonium bicarbonate as fungicide ingredients.

Japanese patent 53090319 describes the application of potassium bicarbonate as an active biocide for the control of fungal diseases common to tomato and cucumber plants.

Japanese patent 53118523 describes the combination of sodium bicarbonate and lecithin as an active agent for the control of agricultural and fruit storage fungus diseases.

Japanese patent 56043207 describes a biocidal composition containing sodium bicarbonate and a polyglycerol fatty acid ester. The biocide controls *Penicillium digitatum* on oranges, *Sphaerotheca fuligenea* on cucumbers, *Piricularia oryzae* on rice, and mosaic virus on tomatoes.

Japanese patent 60097909 describes a soil fungicide prepared by admixing slaked lime with sodium bicarbonate, potassium bicarbonate, boric acid and phenolphthalein.

German patent DE 2927994 describes a fungicide which consists of sodium bicarbonate incorporated into a food-compatible surfactant such as saccharose laurate.

Japanese patent 57062208 describes horticultural fungicides in which the addition of sodium bicarbonate to polyoxin or thiophanatemethyl increases the fungicidal activity of the organic biocide against *botrytis cinerea* on cucumbers.

Japanese patent 58023609 describes an agricultural fungicide composed of a mixture of sodium bicarbonate or potassium bicarbonate with cupric hydroxide, basic copper carbonate or basic copper sulfate. The combination of ingredients exhibits a synergistic fungicidal effect against cucumber early blight, tomato wilt, rice sheath blight, rice blast and citrus canker.

There remains a continuing need for the development of new and more effective fungicides which possess preventive, curative and systemic activity for the protection of cultivated plants, with a minimum of phytotoxic side effects.

Accordingly, it is an object of this invention to provide a dry blend biocide composition which contains a bicarbonate ingredient exhibiting fungicidal properties, and which is harmless to animals and humans.

It is another object of this invention to provide a dry blend fungicide composition which is a non-caking and free-flowing formulation, and which contains particulate ingredients comprising a bicarbonate salt, and a combination of fatty acid salt and hydrophilic polymer which functions as a spreader-sticker and film-forming medium when the composition is diluted with water and applied to plant foliage.

Other objects and advantages of the present invention shall become apparent from the accompanying description and examples.

DESCRIPTION OF THE INVENTION

One or more objects of the present invention are accomplished by the provision of a fungicide composition which is a dry blend formulation comprising (1) an ingredient selected from alkali metal and ammonium bicarbonates; (2) an ingredient selected from alkali metal and ammonium salts of $C_{10}$–$C_{22}$ fatty acids; (3) a film-forming hydrophilic polymer ingredient; and (4) an anti-caking ingredient.

An invention dry blend fungicide composition can contain about 20–85 weight percent of bicarbonate ingredient, about 10–75 weight percent of $C_{10}$–$C_{22}$ fatty acid salt ingredient, about 0.5–20 weight percent of hydrophilic polymer ingredient, and about 0.1–8 weight percent of anti-caking ingredient, based on the composition weight.

A dry blend fungicide composition can be diluted with water to form aqueous fungicidal solutions with controlled rheological properties. An aqueous fungicidal solution typically contains less than about 5 weight percent of active ingredients, based on the solution weight. For most applications the content of bicarbonate ingredient is maintained at a concentration below about one weight percent, as a means of minimizing phytotoxic effects on treated plants which are sensitive to alkaline pH conditions.

An invention dry blend fungicide composition in finely divided form also can be utilized as a dusting powder, which optionally can include a solid diluent such as bentonite, gypsum, diatomaceous earth, and the like. Plant foliage can be treated with a dusting powder, and ambient weather cycles and atmospheric conditions provide sufficient moisture to convert the applied dusting powder to an adherent coating on the plant foliage. A dusting powder preferably has an average particle size diameter between about 1–100 microns, and has a content of submicron particles.

The inorganic salt ingredient of an invention fungicide composition is selected from compounds which include sodium bicarbonate, potassium bicarbonate and ammonium bicarbonate. In a further embodiment, the inorganic salt ingredient can include an additional compound selected from sodium carbonate, potassium carbonate, lithium carbonate and ammonium carbonate, in a quantity of about 1–30 weight percent based on the weight of bicarbonate ingredient.

Illustrative of inorganic salt ingredients in a formulation are sodium, potassium or ammonium bicarbonate; or mixtures such as sodium bicarbonate and potassium bicarbonate; sodium bicarbonate and ammonium bicarbonate; potassium bicarbonate and ammonium bicarbonate; sodium bicarbonate, potassium bicarbonate and ammonium bicarbonate; sodium bicarbonate and potassium carbonate; potassium bicarbonate and potassium carbonate; and the like.

Multiple inorganic salt compounds can be utilized in a broad range of molar quantities relative to each other. The molar quantity of a carbonate salt ingredient normally is determined by pH control considerations when dry blend formulations are being water-diluted. The content of a carbonate salt compound can be varied to control the pH at a desired level in the range of 7.5–12. Water-diluted fungicidal formulations of the present invention tend to have a higher fungicidal activity at higher pH values.

The $C_{10}$–$C_{22}$ fatty acid salt ingredient is selected from alkali metal and ammonium salts of natural straight chain and synthetic branched chain fatty acids, which have a saturated or unsaturated structure. The $C_{10}$–$C_{22}$ fatty acid salt ingredient can be incorporated in a quantity between about 10–75 weight percent, based on the weight of active ingredients in a composition.

Illustrative of natural fatty acids are capric acid, lauric acid, myristic acid, palmitic acid, stearic acid, oleic acid, linoleic acid, arachidic acid, behenic acid, cetoleic acid, and the like.

The $C_{10}$–$C_{22}$ fatty acid salt ingredient can consist of two or more saturated or unsaturated carboxylic acids such as those derived from beef and mutton tallow, lard, cottonseed oil, palm oil, and the like.

Palm fatty acid distillate is a commercial product produced by distilling the fatty acids present in natural palm oil. A distillate product typically has the following weight percent content:

| | |
|---|---|
| Free fatty acids | 60–90 |
| Water | <1 |
| Triglycerides | 10–40 |
| Unsaponifiables | <3 |

The iodine value is less than 54 and the melting point is about 45° C. The content of peroxides is below 10 milliequivalents of oxygen per kilogram. The fatty acids in the free fatty acids and the triglycerides consist of the following weight percent:

| | |
|---|---|
| Palmitic acid | 38–50 |
| Oleic acid | 35–40 |
| Linoleic acid | 5–10 |
| Stearic acid | 3–6 |
| Lauric acid | 1–3 |

Beef tallow acids are available commercially as a byproduct obtained by alkaline extraction of waste beef fat and subsequent acidification, and normally contain the following weight percent of fatty constituents:

| | |
|---|---|
| Free fatty acids | 60–90 |
| Triglycerides | 10–40 |
| Water | <1 |
| Unsaponifiables | <3 |

The iodine value is less than 50 and the melting point is 40°–45° C. The content of peroxides is less than 10 milliequivalents of oxygen per kilogram. The fatty acids in the free fatty acids and in the triglycerides have the following weight percent content:

| | |
|---|---|
| Palmitic acid | 22–28 |
| Oleic acid | 38–44 |
| Linoleic acid | 3–6 |
| Stearic acid | 18–24 |

Because $C_{10}$–$C_{22}$ fatty acids and glycerides are susceptible to atmospheric oxidation, it is advantageous to incorporate an antioxidant, and/or a chelating agent to bind any ferric, copper, zinc or other metal capable of catalyzing atmospheric oxidation. Suitable quantities for inclusion in the fatty acid bulk are about 0.01–0.4% or higher of antioxidant as permitted by regulation, and/or about 0.05–0.3% of chelating agent, based on the weight of fatty acid. Optionally an antioxidant and/or chelating agent can be added to a dry blend or aqueous fungicide composition as additional ingredients during the formulation stage.

Illustrative of preferred additives are butylated hydroxytoluene, butylated hydroxyanisole and tertiary-butylhydroquinone antioxidant, and citric acid and ethylenediamine tetraacetate chelating agents. The chelating agent and antioxidant can be added per se, or in a solvent such as propylene glycol to facilitate incorporation into the fatty acid or formulated ingredients.

The hydrophilic polymer of an invention fungicide composition is selected from organic polymers which exhibit film-forming properties when an aqueous formulation is applied to plant foliage.

The term "hydrophilic" as employed herein refers to a water-soluble or water-dispersible organic polymer which has a solubility of at least one gram per 100 grams of water at 25° C.

Illustrative of hydrophilic organic polymers which exhibit film-forming properties when applied to surfaces in an aqueous medium are gum arabic, gum karaya, gum tragacanth, guar gum, locust bean gum, xanthan gum, carrageenan, alginate salt, casein, dextran, pectin, agar, 2-hydroxyethyl starch, 2-aminoethyl starch, 2-hydroxyethyl cellulose, methyl cellulose, carboxymethyl cellulose salt, cellulose sulfate salt, polyvinylpyrrolidone, polyethylene glycol, polyacrylamide, gelatin, and the like.

Many of the hydrophilic polymers are large volume commercial products. Sodium carboxymethyl cellulose (CMC) is available in powder or granular form having a particle size of 50–200 microns. CMC is available in a degree of substitution (DS) range of 0.38–1.4.

The anti-caking ingredient of an invention fungicide composition is selected from particulate inorganic and organic compounds which are chemically unreactive with the other ingredients when the composition is in the form of a dry blend formulation. A selected compound preferably has a particulate size distribution less than about 100 microns in diameter.

Suitable anti-caking ingredients include silicious compounds, magnesium compounds, $C_{10}$–$C_{22}$ fatty acid polyvalent metal salt compounds, and the like.

Illustrative of anti-caking ingredients are attapulgite clay, kieselguhr, silica aerogel, silica xerogel, perlite, talc, vermiculite, sodium aluminosilicate, ammonium carbonate, zirconium oxychloride, starch, sodium or potassium phthalate, calcium silicate, calcium phosphate, calcium nitride, aluminum nitride, copper oxide, magnesium carbonate, magnesium silicate, magnesium nitride, magnesium phosphate, magnesium oxide, magnesium nitrate, magnesium sulfate, magnesium chloride, and the like.

Preferred anti-caking ingredients include magnesium silicate, and the magnesium, aluminum and calcium salts of $C_{10}$–$C_{22}$ fatty acids such as palmitic acid, stearic acid and oleic acid.

The use of magnesium silicate as an anti-caking ingredient has particular advantage for purposes of the present invention. Magnesium silicate contributes excellent anti-caking and free-flowing properties to an invention dry blend formulation. Also, when a dry blend formulation is water-diluted, the alkaline pH and the presence of alkali metal compounds cause the conversion of some magnesium silicate to alkali metal silicate. The resultant alkali metal silicate exhibits strong adhesive activity when the aqueous formulation is applied to plant foliage.

The anti-caking ingredient normally is utilized in the least quantity which will effect the desired degree of anti-caking and free-flowing properties. Typically the anti-caking ingredient is incorporated in a dry blend formulation in a quantity between about 0.1–2 weight percent, based on the composition weight.

A preferred dry blend fungicide composition of the present invention is one containing sodium or potassium bicarbonate, sodium or potassium oleate, xanthan gum, and magnesium silicate ingredients.

The ingredients in an invention fungicide composition can be selected to include nitrogen, phosphorus and potassium elements in a ratio that qualifies the composition to function as a fertilizer in addition to its function as a fungicide, when applied to cultivated crops. When a water-diluted fungicide composition containing fertilizer elements is sprayed on plant foliage, there is direct absorption of the fertilizer elements into the leaves.

In another embodiment this invention provides a fungicidal fertilizer composition which is a dry blend formulation comprising (1) about 20–85 weight percent of an ingredient selected from alkali metal and ammonium bicarbonates; (2) about 10–75 weight percent of an ingredient selected from alkali metal and ammonium salts of $C_{10}$–$C_{22}$ fatty acids; (3) about 0.5–20 weight percent of a hydrophilic polymer ingredient; (4) about 0.1–8 weight percent of an anti-caking ingredient; and (5) about 20–65 weight percent of an ingredient selected from phosphorus-containing compounds; based on the composition weight; wherein the composition ingredients have a formulated ratio of nitrogen, phosphorus and potassium elements. The formulated ratio depends on the intended application. A typical ratio is 10-15-10.

Besides nitrogen, phosphorus and potassium, an invention fungicidal fertilizer composition can contain trace elements, and other essential elements as exemplified by sulfur as contained in a compound such as sodium bisulfite or thiourea.

A present invention fungicide composition can be prepared by dry-blending the particulate ingredients using conventional equipment. In one method, the bicarbonate, fatty acid salt and hydrophilic polymer are pre-blended, and subsequently the anti-caking ingredient is added to the pre-blend in a rotating type mixer before any agglomeration of particles occurs.

In another method, the anti-caking ingredient is pre-blended with the hydrophilic polymer, and the pre-blend then is admixed with the other particulate ingredients.

Without the incorporation of an anti-caking ingredient, the particulate ingredients of a dry blend fungicide composition tend to agglomerate on standing, and the free-flow character of the composition is diminished.

An invention fungicide composition can include one or more other biologically active ingredients, such as those which exhibit herbicidal, insecticidal or plant growth regulating activity.

A fungicide composition of the present invention has a novel combination of properties for the practice of pesticide control in agricultural and horticultural applications.

The bicarbonate ingredient exhibits fungicidal properties, and the efficiency of any additionally included organic pesticide ingredient usually is enhanced by the presence of the bicarbonate ingredient. A lesser quantity of optional pesticide ingredient can be employed to achieve a desired degree of pest control.

A present invention fungicide composition can be formulated to exhibit no phytotoxicity, or to minimize the toxic effects of salt stress on plants by the bicarbonate ingredient.

A present invention fungicide composition provides particular advantage for the control of infectious phytopathogenic fungi which thrive under acidic soil conditions.

All of the fungicide composition ingredients are biocompatible when the composition is applied in an agricultural environment. The bicarbonate, $C_{10}$–$C_{22}$ fatty acid salt, hydrophilic polymer and anti-caking ingredients are all harmless to animals and humans.

A significant feature of a present invention dry blend fungicide composition is the presence of $C_{10}$–$C_{22}$ fatty acid salt and hydrophilic polymer ingredients, which function as a spreader-sticker medium when the fungicide composition is applied to plant foliage as a water-diluted solution. An applied aqueous solution forms an adherent coating of ingredients on plant foliage or fruit. The fatty acid salt ingredient aids in spreading and sticking the fungicide composition ingredients to the foliage or fruit to which it is applied. The hydrophilic polymer ingredient increases the amount of aqueous fungicide composition which adheres to the plant surfaces because of its static high apparent viscosity. During a spraying procedure, the hydrophilic polymer ingredient contributes a low psuedoplastic viscosity to the spray solution, which facilitates the spraying action. After spraying, the applied coating resists drifting under wind conditions, and exhibits humectant properties in addition to enhanced fungicidal activity.

Another important advantage of a preferred invention fungicide composition derives from the water-solubility of the main ingredients. A coating of an invention fungicide composition on plant foliage or fruit can be removed readily by water-washing. Conventional fungicide compositions which contain a petroleum-based spreader-sticker ingredient leave an oily residue on treated plant foliage or fruit which is difficult to remove.

The following examples are further illustrative of the present invention. The components and specific ingredients are presented as being typical, and various modifications can be derived in view of the foregoing disclosure within the scope of the invention.

EXAMPLE I

This Example illustrates the preparation of a fungicide powder composition in accordance with the present invention.

A free-flowing blend of the following ingredients is prepared in a cone mixer:

| | Parts |
|---|---|
| sodium bicarbonate | 40 |
| potassium bicarbonate | 25 |
| sodium stearate | 25 |
| xanthan gum | 10 |
| calcium silicate | 3 |

The formulated powder is diluted with water by dispersing 2 parts of the powder blend into 100 parts of water. The resulting solution is sprayed onto plant foliage where it forms an adherent coating on the foliage surfaces.

The formulated powder remains free-flowing when it is stored in a closed container at ambient temperature for six months. The same formulation without an anti-caking ingredient undergoes some agglomeration of particles and loss of free-flow capability under the same storage conditions.

EXAMPLE II

This Example illustrates the preparation of a dry blend fungicidal formulation in accordance with the present invention.

| | Parts |
|---|---|
| potassium bicarbonate | 50 |
| potassium oleate | 15 |
| potassium stearate | 10 |
| potassium palmitate | 10 |
| sodium carboxymethyl-cellulose[(1)] | 15 |
| magnesium silicate | 6 |

[(1)]Aldrich Chemical Co., CMC of 3000-6000 centipoises, intrinsic viscosity of 2% aqueous solution at 25° C.

(1) Aldrich Chemical Co., CMC of 3000-6000 centipoises, intrinsic viscosity of 2% aqueous solution at 25° C.

The magnesium silicate is admixed with a pre-blend of the other ingredients to form a non-caking free-flowing powder. The magnesium silicate has an average particle size of about 10 microns.

The powder is suspended in water to form an aqueous emulsion with a 0.3 weight percent content of potassium bicarbonate. The diluted formulation is tested as a fungicide medium against plant foliage infected with powdery mildew. The fungicidal medium is 100% effective in mildew eradication, and prevents re-infection.

EXAMPLE III

This Example illustrates the preparation of a dry blend fungicidal formulation which contains a mixture of bicarbonate compounds and an anti-caking ingredient.

| | Parts |
|---|---|
| potassium bicarbonate | 15 |
| sodium bicarbonate | 15 |
| ammonium bicarbonate | 15 |
| ammonium palmitate | 30 |
| carrageenan | 5 |

-continued

| | Parts |
|---|---|
| sodium phthalate | 2 |

The particulate ingredients are dry blended to form a non-caking free-flowing powder.

The ingredients are added to the water to form an aqueous solution which has a 0.5 weight percent content of bicarbonate ingredients.

The formulation is more effective than a comparative formulation containing a single bicarbonate compound, for controlling a broad range of foliar and soil-born resistant fungi.

EXAMPLE IV

This Example illustrates the preparation of a fungicidal fertilizer composition for application to plant foliage and soil.

| | Parts |
|---|---|
| sodium bicarbonate | 20 |
| potassium oleate | 20 |
| potassium octanoate | 10 |
| xanthan gum | 4 |
| ammonium nitrate | 15 |
| dipotassium orthophosphate | 5 |
| magnesium stearate | 1 |

The zinc sulfide (0.1-10 micron range) is pre-blended with the particulate ammonium nitrate ingredient, and the pre-blend then is combined with the other ingredients in a rotatory mixer to form a non-caking free-flowing powder.

The powder is dispersed in water to form a solution which has a 0.5 weight percent content of potassium bicarbonate.

A container of the solution is connected to agricultural sprayer equipment, and sprayed through a hollow cone spray nozzle at a pressure of 250 psi. The spray droplet size is 100-150 microns. A field of ornamental evergreen saplings is sprayed with the solution, and is effective for preventing fungal infection of the trees, and for promoting vigorous growth.

What is claimed is:

1. A fungicidal fertilizer composition which is a dry blend formulation comprising (1) about 20-85 weight percent of an ingredient selected from alkali metal and ammonium bicarbonates; (2) about 10-75 weight percent of an ingredient selected from alkali metal and ammonium salts of $C_{10}$-$C_{22}$ fatty acids; (3) about 0.5-20 weight percent of a film-forming hydrophilic polymer; (4) about 0.1-8 weight percent of an anti-caking ingredient; and (5) about 20-65 weight percent of an ingredient selected from phosphorus-containing compounds; wherein the composition ingredients have a formulated fertilizer-effective ratio and weight of nitrogen, phosphorus and potassium elements.

2. A composition in accordance, with claim 1 which additionally contains between about 1-30 weight percent of an ingredient selected from alkali metal and ammonium carbonates, based on the weight of bicarbonate ingredient.

3. A composition in accordance with claim 1 which has a content of sulfur-containing ingredient.

4. A composition in accordance with claim 1 which contains sodium bicarbonate, potassium oleate, xanthan gum, ammonium nitrate and potassium phosphate.

5. A composition in accordance with claim 1 which consists of water-soluble ingredients.

* * * * *